United States Patent
Zeng et al.

(10) Patent No.: US 10,816,118 B2
(45) Date of Patent: Oct. 27, 2020

(54) BENDING TUBE

(71) Applicant: Zhuhai Pusheng Medical Science & Technology Co., Ltd, Zhuhai (CN)

(72) Inventors: Guohua Zeng, Zhuhai (CN); Honghui Huang, Zhuhai (CN); Zhenwei Wang, Zhuhai (CN); Jun Wu, Zhuhai (CN)

(73) Assignee: Zhuhai Pusheng Medical Science & Technology Co., Ltd., Zhuhai (CN)

( * ) Notice: Subject to any disclaimer, the term of this patent is extended or adjusted under 35 U.S.C. 154(b) by 231 days.

(21) Appl. No.: 15/847,891

(22) Filed: Dec. 19, 2017

(65) Prior Publication Data

US 2018/0231162 A1 Aug. 16, 2018

(30) Foreign Application Priority Data

Feb. 14, 2017 (CN) .......................... 2017 1 0079500

(51) Int. Cl.
| | |
|---|---|
| *F16L 27/08* | (2006.01) |
| *F16L 11/18* | (2006.01) |
| *A61B 17/29* | (2006.01) |
| *A61B 17/00* | (2006.01) |

(52) U.S. Cl.
CPC ............... *F16L 27/08* (2013.01); *F16L 11/18* (2013.01); *A61B 17/29* (2013.01); *A61B 2017/00314* (2013.01); *A61B 2017/2905* (2013.01)

(58) Field of Classification Search
CPC ....... F16L 27/08; F16L 37/248; F16L 37/252; F16L 27/0804; F16L 27/10; F16L 9/006; F16L 9/22; F16L 11/18
USPC ..................... 285/148.19, 906, 913; 138/120
See application file for complete search history.

(56) References Cited

U.S. PATENT DOCUMENTS

| | | | |
|---|---|---|---|
| 3,253,842 A * | 5/1966 | Rabe | |
| 5,807,241 A * | 9/1998 | Heimberger | |
| 5,857,713 A * | 1/1999 | Horimoto | ................. 285/906 X |
| 8,562,610 B2 * | 10/2013 | Chabansky | |
| 2015/0093184 A1 * | 4/2015 | Henry | |
| 2016/0178098 A1 * | 6/2016 | Felber | |

* cited by examiner

*Primary Examiner* — Zachary T Dragicevich
(74) *Attorney, Agent, or Firm* — Wayne & Ken, LLC; Tony Hom

(57) ABSTRACT

A bending tube including a plurality of structural units (100). Each of the structural units (100) includes a first connecting pipe and a second connecting pipe. One end of the first connecting pipe is provided with a slot and a T-shaped structure, a clamping block and a limiting slot are provided on one end of the second connecting pipe, a first limiting structure (7) is provided on both sides of one end of the limiting slot, and the other end of the limiting slot is provided with a second limiting structure (8); the clamping block and the T-shaped structure are located in the limiting slot, two flanks are provided on the original pin to form a T-shaped structure (6), and the T-shaped structure makes it difficult to disengage the pin, thereby increasing the strength of the bending tube in the direction perpendicular to the bend.

2 Claims, 1 Drawing Sheet

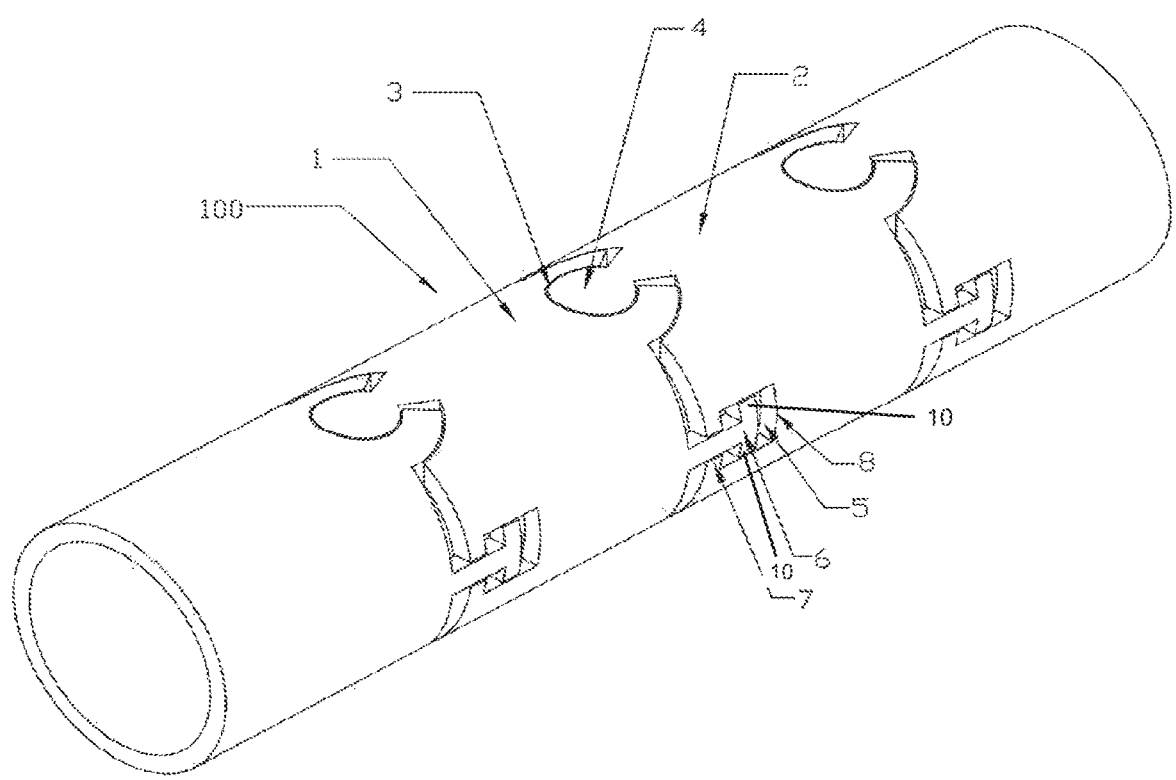

BENDING TUBE

FIELD OF THE INVENTION

The present invention relates to technical field of bending tube, and more specially, relates to a bending tube.

BACKGROUND OF THE INVENTION

Existing bending tube is manufactured by cutting centripetally through certain thickness of the tube and bending through a pair of symmetrical joints with larger outer diameter and smaller inner diameter formed by centripetal cutting, and the trapezoidal surface of the joints can ensure that the joints will not be disengaged in general. However, the strength of the bending tube perpendicular to the bending direction is weak. If one pin is added to strengthen, that is, one pin of a segment of the bending tube is inserted into the groove matched with adjacent segment, two pins are needed and the connection of the pin and the bending surface are suprafacial. The strength perpendicular to bending direction is strengthened with support of this pin, and this pin has no effect on the strength of bending direction. The strengthening effect is limited, when the pin is under slightly greater force, the pin is easily deformed, disengaged with groove and has no effect. The length of the pin can be extended for better reinforcing effect. However, overlong pin after bending will affect on internal space of the bending tube.

SUMMARY OF THE INVENTION

The present invention is to overcome the problems about strength difference of the bending tube perpendicular to the bending direction without reinforcing structure, and great effect on the interior of the bending tube with reinforcing structure by providing a bending tube.

In order to solve the above technical problems, the present invention provides the following technical solutions:

The present invention provides a bending tube, comprising a plurality of structural units, each of the structural units comprises a first connecting pipe and a second connecting pipe, wherein a slot and a T-shaped structure are provided on one end of the first connecting pipe; a clamping block and a limiting slot are provided on one end of the second connecting pipe; a first limiting structure is provided on both sides of one end of the limiting slot, and the other end of the limiting slot is provided with a second limiting structure; the clamping block is located in the slot, and the T-shaped structure is located in the limiting slot; a top end of the second connecting pipe of the structural units is connected with a bottom end of the first connecting pipe of adjacent structural unit, thereby forming a curve tubular-shaped bending tube successively connected by the plurality of structural units.

As a preferred embodiment of the present invention, the horizontal cross sections of the slot and the clamping block are circular.

As a preferred embodiment of the present invention, the horizontal cross sections of the slot and the clamping block are trapezoid.

The beneficial effect of the invention is that the bending tube strengthens the vertical bending direction strength of the bending tube by the T-type structure, the T-type structure is more effective than strip pin and has little effect on the internal structure of the bending tube, and the strength of the bending direction of bone has also been strengthened.

BRIEF DESCRIPTION OF THE DRAWINGS

The accompanying drawings are intended to provide a further understanding of the invention and form a part of the specification, and are intended to be illustrative of the invention in conjunction with the embodiments of the invention and are not to be construed as limiting the invention.

DETAILED DESCRIPTION OF THE INVENTION

Preferred embodiments of the present invention are described with reference to the accompanying drawings, and it is to be understood that the preferred embodiments described herein are only for illustration purpose, and are not intended to limit the invention.

Embodiment 1

As shown in FIG. 1, the present invention provides a bending tube. The bending tube includes a plurality of structural units (100), each of the structural units (100) comprises a first connecting pipe (1) and a second connecting pipe (2). A slot (3) and a T-shaped structure (6) are provided on one end of the first connecting pipe (1); a clamping block (4) and a limiting slot (5) are provided on one end of the second connecting pipe (2); a first limiting structure (7) is provided on both sides of one end of the limiting slot (5), and the other end of the limiting slot (5) is provided with a second limiting structure (8); the clamping block (4) is located in the slot (3), and the T-shaped structure (6) is located in the limiting slot (5); a top end of the second connecting pipe (2) of the structural units (100) is connected with a bottom end of the first connecting pipe (1) of adjacent structural unit (100), thereby forming a curve tubular-shaped bending tube successively connected by the plurality of structural units (100).

The horizontal cross sections of the slot (3) and the clamping block (4) are circular, which reduces the resistance when the bending tube bends and makes it easier to bend. The horizontal cross sections of the slot (3) and the clamping block (4) are trapezoid so that the first connecting pipe (1) and the second connecting pipe (2) are not easily to be disjointed when connecting with clamping block (4) through the clamping block (4).

Specific working principle: two rectangular flanks (10) are provided on the original pin to form a T-shaped structure (6), other positions keep clearance. Each of the two rectangular flanks (10) includes a flat side wall which is in surface-to-surface contact with a flat inner wall of the limiting slot (5). When the bending tube bends to the limiting position, the T-shaped structure (6) stucks or pushes against the limiting position. First of all, the T-shaped structure (6) is a pin in nature, which can strengthen the strength perpendicular to the bending direction. Secondly, in the structure of the bending tube with a pin, when the bones are broken perpendicularly to the bending direction, the pin is bent firstly, then the pin is disengaged, and finally the bending tube is broken, and the T-shaped structure makes it difficult to disengage the pin, thereby increasing the strength of the pin in the direction perpendicular to the bend. And the T-shaped structure (6) is designed to push the limiting position when it is bent to the limiting position, and further bending of the bones can be prevented, and the strength of the bending direction can also be increased. When the bending tube is flat, the T-shaped structure (6) has no effect. When the bending tube is bent, the two T-shaped structures are respectively close to the first limiting structure (7) and the second limiting structure (8); when the bending tube is bent to the limiting position, the T-shaped structure is pushed in place, and the strengthening effect begins to emerge.

The beneficial effect of the invention is that the bending tube strengthens the vertical bending direction strength of the bending tube by the T-type structure, compared with strip pin, the T-type structure is more effective and has little effect on the internal structure of the snake, and the strength of the bending direction of bone has also been strengthened.

It should be noted that the foregoing is only a preferred embodiment of the present invention and is not intended to limit the invention. Although the invention has been described in detail with reference to the foregoing embodiments, it will be apparent to those skilled in the art that the technical solutions described in the foregoing embodiments may be modified or equivalently replaced with some of the technical features therein. Any modifications, equivalent substitutions, improvements and the like within the spirit and principles of the invention are intended to be included within the scope of the present invention.

What is claimed is:

1. A bending tube, comprising: a plurality of structural bending tube units (100), each of the structural bending tube units (100) comprises a first connecting pipe (1) and a second connecting pipe (2);

wherein a pipe wall of the first connecting pipe (1) is provided with an arch-shaped slot (3) and a T-shaped structure (6); a pipe wall of the second connecting pipe (2) is provided with a clamping block (4) and a limiting slot (5); a first limiting structure (7) is provided on both sides of one end of the limiting slot (5), and the other end of the limiting slot (5) is provided with a second limiting structure (8); the clamping block (4) is located inside the arch-shaped slot (3), and the T-shaped structure (6) is located inside the limiting slot (5); a top end of the second connecting pipe (2) of the structural bending units (100) is connected with a bottom end of the first connecting pipe (1) of adjacent structural bending unit (100);

the T-shaped structure (6) comprises two rectangular flanks (10); each of the two rectangular flanks (10) comprises a flat side wall which is in surface-to-surface contact with a flat inner wall of the limiting slot (5).

2. The bending tube of claim 1, wherein the first limiting structure (7) is configured to limit the two rectangular flanks (10) of the T-shaped structure (6) from disengaging from the limiting slot (5).

* * * * *